United States Patent
Donnermeyer et al.

Patent Number: 6,007,707
Date of Patent: Dec. 28, 1999

[54] PROCESS FOR THE RECOVERY OF PURE HYDROCARBONS FROM A HYDROCARBON MIXTURE

[75] Inventors: Stefan Donnermeyer; Jürgen Ludolph; Hans-Jürgen Vollmer, all of Essen, Germany

[73] Assignee: Krupp Uhde GmbH, Dortmund, Germany

[21] Appl. No.: 08/901,361

[22] Filed: Jul. 28, 1997

[30] Foreign Application Priority Data

Jul. 31, 1996 [DE] Germany ............... 196 30 771

[51] Int. Cl.⁶ ........................... B01D 3/40
[52] U.S. Cl. ............ 208/313; 585/865; 585/863; 203/58; 203/59
[58] Field of Search ............ 208/313; 585/865, 585/863; 203/58, 59

[56] References Cited

U.S. PATENT DOCUMENTS

| | | | |
|---|---|---|---|
| 2,376,870 | 5/1945 | Engel ............................ | 203/58 |
| 3,259,555 | 7/1966 | Lankton et al. ................ | 203/63 |
| 3,434,936 | 3/1969 | Luther et al. .................. | 208/313 |
| 3,591,490 | 7/1971 | Muller et al. ................... | 208/313 |
| 4,776,927 | 10/1988 | Emmrich et al. .............. | 208/313 |
| 5,180,474 | 1/1993 | Skatulla et al. ................ | 208/313 |
| 5,238,540 | 8/1993 | Skatulla et al. ................ | 208/313 |
| 5,252,200 | 10/1993 | Skatulla et al. ............... | 208/313 |

FOREIGN PATENT DOCUMENTS

| | | |
|---|---|---|
| 0 491 196 | 6/1992 | European Pat. Off. . |
| 15 43 104 | 9/1969 | Germany . |
| 1543104 | 9/1969 | Germany . |
| 40 40 145 | 6/1992 | Germany . |

*Primary Examiner*—Walter D. Griffin
*Attorney, Agent, or Firm*—Herbert Dubno

[57] ABSTRACT

Process for the recovery of pure hydrocarbons from a hydrocarbon mixture, more particularly, a high aromatics content hydrocarbon mixture, by extractive distillation in an extractive distillation column. A first solvent feed for a first sub-flow of a selective solvent is provided between the top part of the column and the bottom part thereof. The selective solvent used is an N-substituted morpholine. Substantially non-aromatics are withdrawn as the raffinate from the head of the extractive distillation column and substantially aromatics and selective solvent are withdrawn as the extract from the sump of the extractive distillation column. A second sub-flow of the selective solvent is introduced via a second solvent feed in the top part of the column above the first solvent feed. The quantity of solvent supplied with the second sub-flow constitutes less than 50% of the total quantity of solvent.

6 Claims, 2 Drawing Sheets

6,007,707

PROCESS FOR THE RECOVERY OF PURE HYDROCARBONS FROM A HYDROCARBON MIXTURE

FIELD OF THE INVENTION

The present invention relates to a process for the recovery of pure hydrocarbons from a hydrocarbon mixture which contains aromatics and non-aromatics. More particularly this invention relates to the separation of a high-aromatics-content hydrocarbon mixture.

BACKGROUND OF THE INVENTION

The extractive distillation of different aromatics and non-aromatics contained in hydrocarbon mixtures with an N-substituted morpholine as a selective solvent is used to a significant extent in large-scale plants for the recovery of very pure aromatics.

Reformate gasoline, pyrolysis gasoline or crude coke-oven benzene are particularly used as hydrocarbon mixtures. In addition to various aromatics, these hydrocarbon mixtures also contain nonaromatics, which can include paraffins, cycloparaffins, olefins, diolefins and organic sulphur compounds.

By means of extractive distillation the hydrocarbon mixtures are separated into aromatics, on the one hand, and non-aromatics, on the other hand. To this extent this extractive distillation is suitable both for the recovery of pure aromatics and for the recovery of pure non-aromatics, e.g. olefins and diolefins.

In extractive distillation, the aromatics from the hydrocarbon mixture used are concentrated as the extract with the main quantity of the selective solvent in the sump of the extractive distillation column. The non-aromatics from the hydrocarbon mixture used, on the other hand, are concentrated as the raffinate in the head of the extractive distillation column. However, the result of this is that the raffinate occurring at the head of the extractive distillation column still contains significant solvent residues. This solvent component in the raffinate is largely recovered in these extractive distillation processes in a complex and expensive manner.

In the process described in (DE 40 40 145 A1) by contrast with the other known process, both the extractive distillation and the removal of the solvent residues from the raffinate are performed in a single column. For this purpose, the extractive distillation column comprises an additional top column part and the selective solvent is fed to the extractive distillation column via a solvent feed below this upper part of the column. This solvent introduced flows down over the column trays, and in so doing it entrains the aromatics to the sump of the extractive distillation column. The non-aromatic hydrocarbons from the mixture used, on the other hand, rise in vapor form in the extractive distillation column. The top part of the column above the solvent feed serves to enable the solvent residues to be removed from these non-aromatic hydrocarbons. The process known from DE 40 40 145 A1 has proved to be substantially satisfactory, but is open to improvement.

For example, this known process has disadvantages particularly when the hydrocarbon mixture used has a higher aromatics content, e.g. crude coke-oven benzene having an aromatics content of about 85% of pre-purified benzene having an aromatics content of more than 95%. With hydrocarbon mixtures of this kind, the proportion of non-aromatics is very small in relation to the quantity of selective solvent.

In extractive distillation, the aromatics are entrained to the sump of the extractive distillation column by the selective solvent added from above. The non-aromatics rise, as has already been stated, in vapor form to the head of the extractive distillation column. Individual equilibria occur on the individual trays of the extractive distillation column and are dependent particularly on the temperature and on the concentrations of the substances.

These equilibria are disturbed, in the extractive distillation of the known process by irregularities in the column heating or variations in the predetermined solvent temperature or upon changes in the quantity of solvent supplied. These disturbed equilibria have a significant effect on the extractive distillation of a hydrocarbon mixture which has a very high aromatics content, e.g. prepurified benzene having an aromatics content of more than 95%.

Because of the high aromatics content and the low non-aromatics content, particularly in relation to the quantity of selective solvent used, these fluctuations or disturbances cause the aromatics present in high concentration to be no longer completely entrained into the sump by the selective solvent as a result of disturbed equilibria. In particular, low-boiling benzene, which by comparison with the non-aromatics has a lower boiling temperature, can pass to the top part of the column above the solvent feed. As a result, benzene and other low boiling aromatics can reach the head of the extractive distillation column so that a mixture of aromatics and non-aromatics tends to form at the head of the column. Even a small quantity of aromatics reaching the upper part of the column (above the first solvent feed) because of the above fluctuations results in relatively higher aromatics contents in the raffinate when relatively small quantities of non-aromatics are involved. In addition, the aromatics reaching the column head also have an adverse effect on the aromatics yield.

OBJECT OF THE INVENTION

It is the object of the invention to provide an improved extraction distillation process wherein despite irregularities and fluctuations in extractive distillation conditions, particularly temperature and concentration fluctuations, a clean separation of aromatics and non-aromatics can be obtained with a correspondingly high yield of aromatics and non-aromatics in a relatively simple and inexpensive manner.

SUMMARY OF THE INVENTION

The invention is an improvement in separation by extractive distillation in an extractive distillation column, wherein a first sub-flow of a selective solvent is fed to the extractive distillation column between a top part and a bottom part of the column via a first solvent feed, wherein at least one N-substituted morpholine is used as selective solvent and wherein substantially non-aromatics are withdrawn as the raffinate from the top of the extractive distillation column and substantially aromatics and selective solvent are withdrawn as the extract from the sump of the extractive distillation column.

According to the invention a second sub-flow of the selective solvent is introduced into the extractive distillation column via a second solvent feed in the top part of the column above the first solvent feed, and the quantity of solvent supplied with the second sub-flow is less than 50% of the total quantity of solvent supplied with the first and second subflows.

According to the invention, more particularly, a high aromatics content hydrocarbon mixture i.e. a mixture with an aromatics content of above 85%, is used for the process according to the invention. Preferably, pre-purified benzene having an aromatics content of more than 95% and/or crude coke-oven benzene having an aromatics content of about 85% are used.

According to a feature of the invention, also, it is possible to use pyrolysis gasoline, having an aromatics content of about 35%. Of course, mixtures of such feed stocks can be used in the process according to the invention.

As a rule, the hydrocarbon mixtures particularly comprise aromatics having 6 to 8 carbon atoms. Preferably, N-substituted morpholines having not more than 7 carbon atoms in the substituent are used as the selective solvent. In a preferred embodiment of the invention, N-formylmorpholine is used as the selective solvent.

The invention is based on the realization that in the process known from DE 40 40 145 A1, there is no selective solvent supplied in the part of the column above the solvent feed and therefore in this part of the column the prevailing conditions are substantially distillation conditions and not extractive distillation conditions. For this reason, for example, light-boiling benzene can pass into the head of the column in the event of the above-described fluctuations in extractive distillation conditions, and the benzene is therefore adversely mixed with the non-aromatics in the head.

The invention is further based on the realization that if a second sub-flow of selective solvent is supplied via a second solvent feed disposed above the first solvent feed, extractive distillation conditions can be created in the zone between the two solvent feeds.

This additional portion of the column in which extractive distillation conditions apply enables aromatics and, in particular, benzene, to be prevented from entering the head of the column. The aromatics are washed back to the bottom part of the column. Even in the event of relatively considerable fluctuations in temperatures and concentrations in the extractive distillation column, this result is achieved by the additional extractive distillation zone between the two solvent feeds. For this purpose it is, surprisingly, sufficient to supply only a relatively small quantity of selective solvent via the second solvent feed.

The quantity of solvent supplied via the second solvent feed should be less than 50% of the total quantity of the solvent. Preferably, this quantity of solvent constitutes only about 0.5 to 10% of the total quantity.

It is indeed surprising that the aromatics can be effectively kept away from the head of the column by supplying relatively small quantities of selective solvent via the second solvent feed. Because of the additional solvent sub-flow, fluctuations in respect of temperature and the quantity of solvent supplied have practically no effect on the aromatics content in the column head.

The relatively small quantity of solvent allows more accurate adjustment and regulation for the second sub-flow.

Heat can be supplied, e.g. via a boiler, between the top part and the bottom part of the extractive distillation column.

The result with the process according to the invention is a clean separation of aromatics, which are recovered from the column sump, and non-aromatics which are recovered from the column head. Accordingly, a high yield is obtained both of pure aromatics and pure non-aromatics. It should be stressed that these advantages can be obtained in a simple and inexpensive manner.

By comparison with the extractive distillation column used in the process according to DE 40 40 145 A1, the extractive distillation column used according to the invention need be increased by only about 5 to 10 theoretical trays or separating stages. Apart from the second solvent feed, no further apparatus is required for the plant. In comparison with the known process, there is no need for additional quantities of selective solvent, since with the process according to the invention the quantity of solvent used is simply divided into two sub-flows which are introduced into the extractive distillation column via the two solvent feeds.

Of course, according to the process of the invention there is disposed between the second solvent feed and the head of the extractive distillation column a portion of the top part of the column in which distillation conditions obtain and which serves for distillation separation of the selective solvent from the nonaromatics.

According to the invention, it is possible for the extract of aromatics and selective solvent withdrawn from the sump of the extractive distillation column to be fed to a stripper column and for the aromatics to be separated from the selective solvent in the stripper column. Advantageously, the stripper column is operated in vacuo and the aromatics product in these conditions is obtained in the head of the stripper column. The selective solvent is transferred to the sump of the stripper column.

According to a preferred embodiment of the invention, the selective solvent withdrawn from the extractive distillation column sump is recycled and re-introduced into the extractive distillation column via the solvent feeds. For this purpose, the selective solvent obtained in the stripper column sump is advantageously returned to the extractive distillation column via the first and second solvent feeds.

Advantageously, the solvent withdrawn from the stripper column is fed through a suitable heat exchanger in order to cool the selective solvent and set the required solvent temperature. Preferably, the quantity of solvent supplied with the second sub-flow via the second solvent feed constitutes 0.5 to 10% of the total quantity of solvent supplied with the first and second sub-flow.

According to the invention also, the hydrocarbon mixture used can also be evaporated in a separating tank before being introduced into the extractive distillation column and thus can be split into a liquid and vapor phase. The two phases can then be fed to the extractive distillation column separately from one another. In these conditions, the vapor phase is introduced into the extractive distillation column beneath the feed for the liquid phase.

Of course with the process according to the invention the temperature of the selective solvent supplied and the temperature of the hydrocarbon mixture introduced can be adjusted by means of appropriate heat-exchangers. The heating of the extractive distillation column is effected in the conventional manner.

The method of the invention thus comprises the steps of:
(a) subjecting the mixture to extractive distillation with a selective solvent comprising an N-substituted morpholine in an extractive distillation column to which the selective solvent is fed at a first solvent feed location between a head of the column and a sump thereof, whereby nonaromatics are withdrawn as a raffinate at the head of the column and aromatics and the selective solvent collect in the sump;
(b) withdrawing the aromatics and selective solvent collected in the sump and separating the aromatics from the selective solvent;
(c) introducing a second sub-flow of the selective solvent into the column at a second solvent feed location at an upper part of the column above the first feed location; and (d) controlling the flow rate of the second sub-flow so that it constitutes less than 50% of a total flow rate of the selective solvent into the column at the first and second solvent feed locations.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
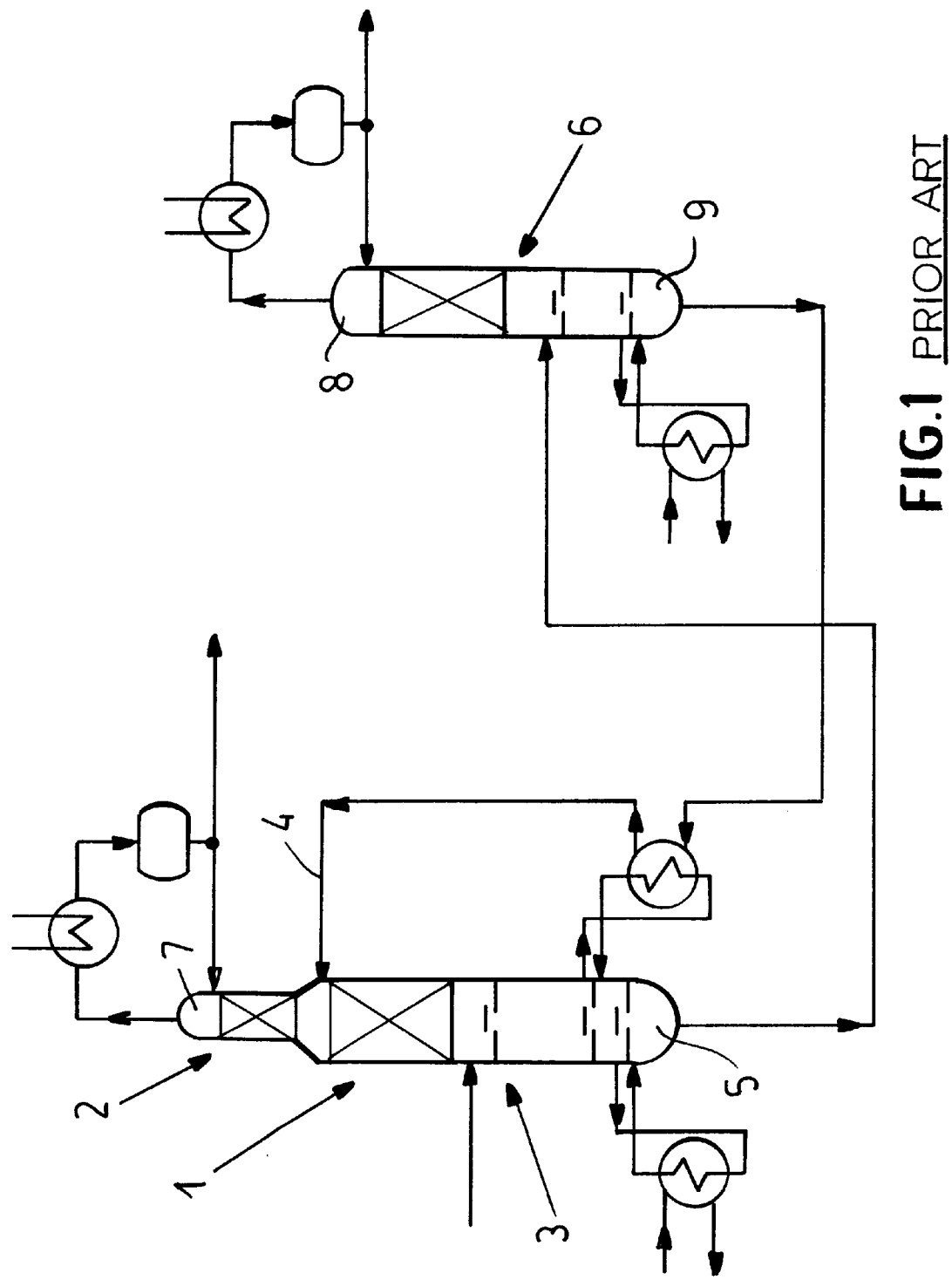
FIG. 1 is a diagram of apparatus for the recovery of hydrocarbons according to the prior art.
Figure 2:
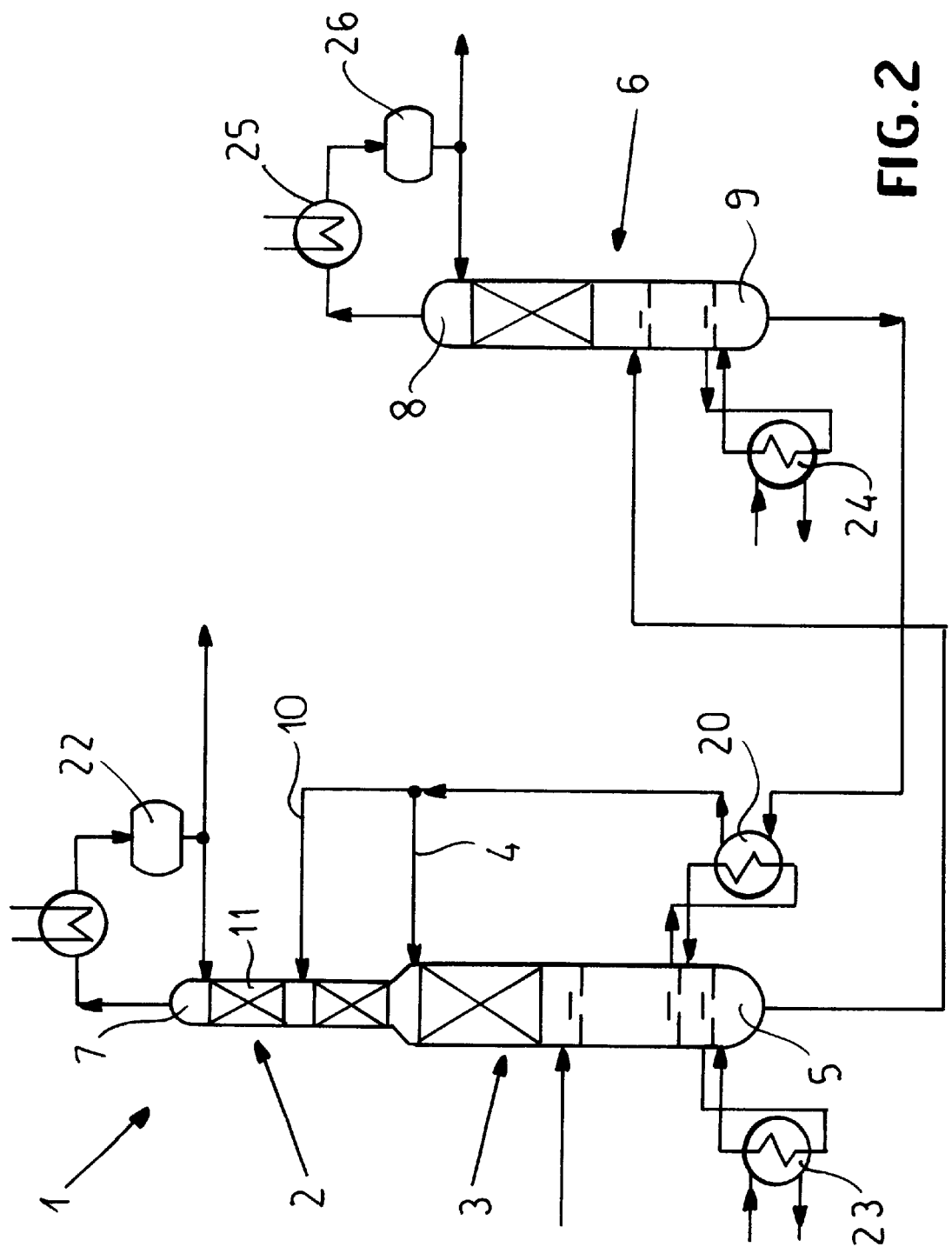
FIG. 2 is a diagram of apparatus for performing the process of the invention for the recovery of pure hydrocarbons.

FIGS. 1 and 2 show systems for performing processes for the recovery of pure hydrocarbons from the hydrocarbon mixture which contains aromatics and nonaromatics, more particularly from a high-aromatics content hydrocarbon mixture.

In the processes, extractive distillation takes place in an extractive distillation column 1, wherein a solvent feed 4 is admitted between a column top part 2 and a column bottom part 3, the selective solvent being introduced into the extractive distillation column 1 via said feed 4. The column top part 2 can be constructed as a separate column.

N-formylmorpholine is preferably used as a selective solvent.

As a result of the addition of the selective solvent to the extractive distillation column 1, the boiling points of aromatics and non-aromatics in the hydrocarbon mixture used are so shifted relative to one another that they can be separated in the extractive distillation column. The aromatics are carried by the selective solvent to the sump 5 of the extractive distillation column 1.

The extract of aromatics and selective solvent obtained in the sump 5 of the extractive distillation column 1 is withdrawn and fed to a stripper column 6.

The non-aromatics rise in the form of vapor in the extractive distillation column and are obtained as the raffinate in the head 7 of the extractive distillation column 1 from which they can be removed.

In the stripper column 6, the extract of aromatics and selective solvent withdrawn from the sump 5 is preferably separated in vacuo into aromatics and the selective solvent. The aromatics are obtained in the head 8 of the stripper column 6, and can be withdrawn from there.

The selective solvent collects in the sump 9 of the stripper column 6. The selective solvent is withdrawn from the sump 9 and recycled to the extractive distillation column 1 via the solvent feed 4, 10. The selective solvent is thus recycled. Of course suitable heat-exchangers (e.g. heat exchanger 20) are provided to cool the selective solvent to a predetermined temperature before re-introduction into the extractive distillation column 1. Both in FIG. 1 and FIG. 2 the column top part 2 disposed above the solvent feed 4 is constructed as a column superstructure which frequently has a smaller diameter than the bottom part 3 of the extractive distillation column 1.

FIG. 1 shows the apparatus for performing the process according to DE 40 40 145 A1. Here only a single solvent feed 4 is provided between the column top part 2 and the column bottom part 3. Substantially nonextractive distillation conditions obtain in the column top part 2 above the solvent feed 4 and this column top part serves for removal of the selective solvent from the non-aromatics which accumulate in the head 7 of the column. As already explained above, this process is distinguished by the disadvantage that in the event of fluctuations in the extractive distillation conditions, more particularly fluctuations in the heating of the extractive distillation column 1, the solvent temperature and/or the quantity of selective solvent supplied, aromatics may enter the top part 2 of the column and undesirably mix with the non-aromatics in the head 7. This disadvantageous effect occurs particularly if high-aromatics-content hydrocarbon mixtures are used in the known process.

FIG. 2 shows an apparatus for performing the process according to the invention. According to the invention, a second or sub-flow of the selective solvent is fed to the extractive distillation column 1 via a second solvent feed 10 in the top part 2 of the column above the first solvent feed 4. The quantity of solvent feed with the second or sub-flow is preferably only 0.5 to 10% of the total quantity of solvent feed via the solvent feeds 4 and 10.

Surprisingly, as a result of this relatively inexpensive step, the aromatics pass to the sump 5 of the extractive distillation column 1 practically completely, even the event of the above-described fluctuations in the extractive distillation conditions, and the non-aromatics accordingly are obtained with greater purity in the head 7 of the extractive distillation column. These advantages are achieved particularly even in the case of hydrocarbon mixtures having a non-aromatics contents below 15% and especially below 5%.

Another column portion 11 of the top part 2 of the column is disposed above the second solvent feed 10 shown in FIG. 2 and serves to remove the selective solvent from the non-aromatics distillatively. A condenser can be provided at 21 and from the liquid collected at 22, a portion can be recycled to the head 7 while another portion is led away. The heat input to the sump of the extractive distillation column is represented by the heat exchanger 23 while a similar heat exchanger 24 supplies heat to boil the sump liquid in the stripper 6. The latter has a condenser 25 and a condensate collector 26. with the process according to the invention, the result is that both aromatics and non-aromatics are obtained in a high yield and high purity. In comparison with the known process, there is no need for an additional recycled quantity of solvent. The process can also be carried out generally with a relatively low specific energy consumption.

We claim:

1. A process for recovering pure aromatic hydrocarbons and pure non-aromatic hydrocarbons from a hydrocarbon mixture containing aromatic hydrocarbons and non-aromatic hydrocarbons, said process comprising the steps of:

(a1) feeding a hydrocarbon mixture containing aromatic hydrocarbons and non-aromatic hydrocarbons and having an aromatics content above 85% to an extractive distillation column which comprises a bottom column part and a top column part of a smaller diameter than that of the bottom column part for removal of solvent residues wherein the hydrocarbon mixture is fed at a given location to the bottom column part of the extractive distillation column;

(a2) feeding a selective solvent comprising an N-substituted morpholine to the extractive distillation column at a first solvent feed location below the top column part and above the given location where the hydrocarbon mixture is fed to said bottom column part of said extractive distillation column;

(a3) subjecting said hydrocarbon mixture to extractive distillation with the selective solvent in the extractive distillation column, whereby pure non-aromatic hydrocarbons are withdrawn from the hydrocarbon mixture as a raffinate at a head above the top column part and pure aromatic hydrocarbons and the selective solvent collect in a sump below the bottom column part;

(b) withdrawing the pure aromatic hydrocarbons and the selective solvent collected in said sump and separating the pure aromatic hydrocarbons from the selective solvent;

(c) introducing a sub-flow of said selective solvent into the column at a second solvent feed location in the top column part above said first solvent feed location; and (d) controlling the flow rate of said sub-flow of said selective solvent introduced at said second solvent feed location so that the sub-flow constitutes 0.5 to 10% of total flow rate of the selective solvent into the extractive distillation column at the first and second solvent feed locations.

2. The process defined in claim 1 wherein said N-substituted-morpholine has a substituent containing at most 7 carbon atoms.

3. The process defined in claim 2 wherein said selective solvent is N-formyl-morpholine.

4. The process defined in claim 1 wherein the aromatics and selective solvent in step (b) withdrawn from said sump of said extractive distillation column are fed to a stripper column from which the aromatics are removed as a head product and the selective solvent is collected at a sump of said stripper column.

5. The process defined in claim 4, further comprising the step of recycling the selective solvent from said sump in said stripper column to said extractive distillation column through said feeds.

6. The process defined in claim 4, further comprising the step of recycling the selective solvent from said stripper column to said feeds in said extractive distillation column.

* * * * *